(12) United States Patent
Voegele et al.

(10) Patent No.: US 7,658,305 B2
(45) Date of Patent: Feb. 9, 2010

(54) ADHESIVE APPLIER WITH ARTICULATING TIP

(75) Inventors: James Walden Voegele, Cincinnati, OH (US); Mark S. Ortiz, Milford, OH (US); Fredrick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 643 days.

(21) Appl. No.: 11/552,669

(22) Filed: Oct. 25, 2006

(65) Prior Publication Data

US 2008/0103452 A1   May 1, 2008

(51) Int. Cl.
*A61B 1/015* (2006.01)
*A61M 5/145* (2006.01)

(52) U.S. Cl. .............. 222/387; 222/533; 604/95.04; 604/187

(58) Field of Classification Search ............ 222/533, 222/387; 604/95.04, 95.05, 187, 528
See application file for complete search history.

(56) References Cited

U.S. PATENT DOCUMENTS

| | | | | |
|---|---|---|---|---|
| 982,661 | A * | 1/1911 | Dickens | 222/387 |
| 1,695,263 | A * | 12/1928 | Jacques | 222/527 |
| 1,705,443 | A * | 3/1929 | Edelmann | 222/533 |
| 1,761,127 | A * | 6/1930 | Jacques | 222/256 |
| 2,776,168 | A * | 1/1957 | Schweda | 239/587.4 |
| 4,735,616 | A | 4/1988 | Eibl et al. | |
| 4,766,898 | A | 8/1988 | Hardy et al. | |
| 4,826,087 | A * | 5/1989 | Chinery | 604/95.04 |
| 4,874,368 | A | 10/1989 | Miller et al. | |
| 5,004,469 | A | 4/1991 | Palmieri et al. | |
| 5,154,320 | A | 10/1992 | Bolduc | |
| 5,254,113 | A | 10/1993 | Wilk | |
| 5,312,333 | A | 5/1994 | Churinetz et al. | |
| 5,318,008 | A * | 6/1994 | Bullard | 600/139 |
| 5,324,305 | A | 6/1994 | Kanner | |

(Continued)

FOREIGN PATENT DOCUMENTS

EP    0315222 B1    11/1992

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner*—Kenneth Bomberg
(74) *Attorney, Agent, or Firm*—Frost Brown Todd LLC

(57) ABSTRACT

An exemplary adhesive applier comprises a handle portion, a shaft portion, and a tip portion. The handle portion is configured to be gripped by a user. The shaft portion is in communication with the handle portion. The tip portion is in communication with the shaft portion. The tip portion is operable to articulate relative to the shaft portion in response to user input, and is operable to dispense a liquid substance at a plurality of articulated positions. In some embodiments, the handle portion is configured to pivot relative to the shaft portion, and the tip portion is operable to pivot relative to the shaft portion in response to pivoting of the handle portion relative to the shaft portion.

9 Claims, 7 Drawing Sheets

U.S. PATENT DOCUMENTS

| | | |
|---|---|---|
| 5,372,585 A | 12/1994 | Tiefenbrun et al. |
| 5,443,481 A | 8/1995 | Lee |
| 5,474,540 A | 12/1995 | Miller et al. |
| 5,520,678 A * | 5/1996 | Heckele et al. .................. 606/1 |
| 5,529,577 A | 6/1996 | Hammerslag |
| 5,582,596 A | 12/1996 | Fukunaga et al. |
| 5,605,541 A | 2/1997 | Holm |
| 5,718,711 A | 2/1998 | Berenstein et al. |
| 5,752,965 A | 5/1998 | Francis et al. |
| 5,759,169 A | 6/1998 | Marx |
| 5,759,171 A | 6/1998 | Coelho et al. |
| 5,814,022 A | 9/1998 | Antanavich et al. |
| 5,842,973 A * | 12/1998 | Bullard ........................ 600/194 |
| 5,844,087 A | 12/1998 | Zimmerman et al. |
| 5,895,412 A | 4/1999 | Tucker |
| 5,928,611 A | 7/1999 | Leung |
| 5,981,621 A | 11/1999 | Clark et al. |
| 6,007,515 A | 12/1999 | Epstein et al. |
| 6,010,714 A | 1/2000 | Leung et al. |
| 6,055,828 A | 5/2000 | Rivera et al. |
| 6,099,807 A | 8/2000 | Leung |
| 6,113,571 A | 9/2000 | Zinger et al. |
| 6,143,352 A | 11/2000 | Clark et al. |
| 6,143,805 A | 11/2000 | Hickey et al. |
| 6,162,239 A | 12/2000 | Manhes |
| 6,174,919 B1 | 1/2001 | Hickey |
| 6,183,593 B1 | 2/2001 | Narang et al. |
| 6,206,905 B1 | 3/2001 | Holm et al. |
| 6,217,603 B1 | 4/2001 | Clark et al. |
| 6,228,051 B1 | 5/2001 | Trumbull |
| 6,234,994 B1 | 5/2001 | Zinger |
| 6,245,933 B1 | 6/2001 | Malofsky et al. |
| 6,280,399 B1 | 8/2001 | Rossin et al. |
| 6,283,933 B1 | 9/2001 | D'Alessio et al. |
| 6,302,898 B1 | 10/2001 | Edwards et al. |
| 6,306,243 B1 | 10/2001 | Clark et al. |
| 6,310,166 B1 | 10/2001 | Hickey et al. |
| 6,322,852 B1 | 11/2001 | Leung |
| 6,325,810 B1 | 12/2001 | Hamilton et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,394,975 B1 | 5/2002 | Epstein |
| 6,394,982 B1 | 5/2002 | Ehrenfels |
| 6,398,797 B2 | 6/2002 | Bombard et al. |
| 6,412,639 B1 | 7/2002 | Hickey |
| 6,420,590 B1 | 7/2002 | Badejo et al. |
| 6,425,704 B2 | 7/2002 | Voiers et al. |
| 6,428,233 B1 | 8/2002 | Clark et al. |
| 6,428,234 B1 | 8/2002 | Bobo et al. |
| 6,432,084 B1 | 8/2002 | Levinson et al. |
| 6,433,096 B1 | 8/2002 | Hickey et al. |
| 6,439,789 B1 | 8/2002 | Balance et al. |
| 6,454,739 B1 | 9/2002 | Chang |
| 6,455,064 B1 | 9/2002 | Narang et al. |
| 6,458,095 B1 | 10/2002 | Wirt et al. |
| 6,461,361 B1 | 10/2002 | Epstein |
| 6,461,367 B1 | 10/2002 | Kirsch et al. |
| 6,464,663 B1 | 10/2002 | Zinger |
| 6,468,520 B1 | 10/2002 | Rowe et al. |
| 6,471,670 B1 | 10/2002 | Enrenfels et al. |
| 6,478,191 B1 | 11/2002 | D'Alessio et al. |
| 6,488,197 B1 | 12/2002 | Whitman |
| 6,488,650 B1 | 12/2002 | Epstein et al. |
| 6,488,944 B2 | 12/2002 | Narang |
| 6,491,201 B1 | 12/2002 | Whitman |
| 6,494,896 B1 | 12/2002 | D'Alessio et al. |
| 6,512,023 B1 | 1/2003 | Malofsky et al. |
| 6,527,749 B1 | 3/2003 | Roby et al. |
| 6,540,716 B1 | 4/2003 | Holm |
| 6,547,467 B2 | 4/2003 | Quintero |
| 6,565,840 B1 | 5/2003 | Clark et al. |
| 6,575,940 B1 | 6/2003 | Levinson et al. |
| 6,579,469 B1 | 6/2003 | Nicholson et al. |
| 6,585,967 B2 | 7/2003 | Narang et al. |
| 6,589,269 B2 | 7/2003 | Zhu et al. |
| 6,592,281 B2 | 7/2003 | Clark et al. |
| 6,595,940 B1 | 7/2003 | D'Alessio et al. |
| 6,602,496 B2 | 8/2003 | Hedgpeth et al. |
| 6,605,667 B1 | 8/2003 | Badejo et al. |
| 6,607,631 B1 | 8/2003 | Badejo et al. |
| 6,613,020 B1 | 9/2003 | Holm et al. |
| 6,616,019 B2 | 9/2003 | D'Alessio et al. |
| 6,620,846 B1 | 9/2003 | Jonn et al. |
| 6,637,967 B2 | 10/2003 | Bobo et al. |
| 6,666,873 B1 | 12/2003 | Cassell |
| 6,676,322 B1 | 1/2004 | Leung |
| 6,681,979 B2 | 1/2004 | Whitman |
| 6,695,199 B2 | 2/2004 | Whitman |
| 6,705,790 B2 | 3/2004 | Quintero et al. |
| 6,743,858 B2 | 6/2004 | Hickey et al. |
| 6,746,667 B2 | 6/2004 | Badejo et al. |
| 6,748,950 B2 | 6/2004 | Clark et al. |
| 6,764,467 B1 | 7/2004 | Roby et al. |
| 6,767,552 B2 | 7/2004 | Narang |
| 6,779,657 B2 | 8/2004 | Mainwaring et al. |
| 6,783,514 B2 | 8/2004 | Tovey et al. |
| 6,802,416 B1 | 10/2004 | D'Alessio et al. |
| 6,802,822 B1 | 10/2004 | Dodge |
| 6,811,341 B2 | 11/2004 | Crane |
| D500,085 S | 12/2004 | Cotter et al. |
| 6,837,027 B2 | 1/2005 | Hickey |
| 6,863,660 B2 | 3/2005 | Marx |
| 6,884,232 B1 | 4/2005 | Hagmann et al. |
| 6,896,684 B2 | 5/2005 | Monassevitch et al. |
| 6,896,838 B2 | 5/2005 | D'Alessio |
| 6,921,381 B2 | 7/2005 | Spero et al. |
| 6,942,875 B2 | 9/2005 | Hedgpeth |
| 6,960,040 B2 | 11/2005 | D'Alessio et al. |
| 7,037,344 B2 | 5/2006 | Kagan et al. |
| 7,044,937 B1 * | 5/2006 | Kirwan et al. .......... 604/167.03 |
| 2002/0012678 A1 | 1/2002 | Narang |
| 2002/0037310 A1 | 3/2002 | Jonn et al. |
| 2002/0048480 A1 | 4/2002 | D'Alessio et al. |
| 2002/0055573 A1 | 5/2002 | Malofsky et al. |
| 2002/0065336 A1 | 5/2002 | Hickey et al. |
| 2002/0119184 A1 | 8/2002 | Nicholson et al. |
| 2002/0147462 A1 | 10/2002 | Mair et al. |
| 2002/0156203 A1 | 10/2002 | Hickey et al. |
| 2002/0157675 A1 | 10/2002 | Clark et al. |
| 2002/0165483 A1 | 11/2002 | Miller et al. |
| 2002/0173770 A1 | 11/2002 | Flory et al. |
| 2002/0176732 A1 | 11/2002 | Quintero et al. |
| 2002/0176733 A1 | 11/2002 | Clark et al. |
| 2002/0185396 A1 | 12/2002 | Mainwaring et al. |
| 2002/0192011 A1 | 12/2002 | Bobo et al. |
| 2002/0192107 A1 | 12/2002 | Hickey |
| 2003/0007826 A1 | 1/2003 | Badejo et al. |
| 2003/0007946 A1 | 1/2003 | Narang et al. |
| 2003/0007947 A1 | 1/2003 | Narang |
| 2003/0007948 A1 | 1/2003 | Hedgpeth |
| 2003/0007949 A1 | 1/2003 | Hedgpeth et al. |
| 2003/0015557 A1 | 1/2003 | D'Alessio et al. |
| 2003/0031499 A1 | 2/2003 | Heard et al. |
| 2003/0032833 A1 | 2/2003 | Badejo et al. |
| 2003/0039781 A1 | 2/2003 | D'Alessio et al. |
| 2003/0044219 A1 | 3/2003 | Quintero |
| 2003/0060380 A1 | 3/2003 | Ayarza et al. |
| 2003/0063944 A1 | 4/2003 | Leung |
| 2003/0080151 A1 | 5/2003 | D'Alessio et al. |
| 2003/0082116 A1 | 5/2003 | Badejo et al. |
| 2003/0096069 A1 | 5/2003 | D'Alessio |
| 2003/0149128 A1 | 8/2003 | Malofsky et al. |

| | | | |
|---|---|---|---|
| 2003/0181964 A1 | 9/2003 | Sharkey et al. | |
| 2003/0202956 A1 | 10/2003 | Clark et al. | |
| 2004/0026282 A1 | 2/2004 | D'Alessio et al. | |
| 2004/0059283 A1 | 3/2004 | Kirwan et al. | |
| 2004/0111115 A1 | 6/2004 | Maw | |
| 2004/0120849 A1 | 6/2004 | Stewart et al. | |
| 2004/0137067 A1 | 7/2004 | Narang et al. | |
| 2004/0143290 A1 | 7/2004 | Brightbill | |
| 2004/0151688 A1 | 8/2004 | Sherbondy et al. | |
| 2004/0190975 A1 | 9/2004 | Goodman et al. | |
| 2004/0223932 A1 | 11/2004 | Hedgpeth et al. | |
| 2004/0223946 A1 | 11/2004 | Kidd et al. | |
| 2004/0234578 A1 | 11/2004 | Chen et al. | |
| 2004/0236316 A1 | 11/2004 | Danitz et al. | |
| 2004/0254561 A1 | 12/2004 | Stenton | |
| 2005/0033328 A1 | 2/2005 | Laufer et al. | |
| 2005/0042266 A1 | 2/2005 | Narang | |
| 2005/0047846 A1 | 3/2005 | Narang et al. | |
| 2005/0070935 A1 | 3/2005 | Ortiz | |
| 2005/0145671 A1 | 7/2005 | Viola | |
| 2005/0147457 A1 | 7/2005 | Badejo et al. | |
| 2005/0175395 A1 | 8/2005 | Quintero et al. | |
| 2005/0182443 A1 | 8/2005 | Jonn et al. | |
| 2005/0184121 A1 | 8/2005 | Heinrich | |
| 2005/0220849 A1 | 10/2005 | Hickey | |
| 2005/0228446 A1 | 10/2005 | Mooradian et al. | |
| 2005/0230453 A1 | 10/2005 | Viola | |
| 2005/0256446 A1 | 11/2005 | Criscuolo et al. | |
| 2005/0273084 A1 | 12/2005 | Hinman et al. | |
| 2006/0009099 A1 | 1/2006 | Jonn et al. | |

FOREIGN PATENT DOCUMENTS

| | | |
|---|---|---|
| EP | 0716833 A2 | 6/1996 |
| EP | 0738 498 | 10/1996 |
| EP | 0648510 B1 | 11/1998 |
| EP | 0669100 B1 | 11/1998 |
| EP | 1078600 A2 | 2/2001 |
| EP | 1159081 A1 | 12/2001 |
| EP | 1381321 A2 | 1/2004 |
| EP | 1113839 B1 | 11/2004 |
| EP | 1073484 B1 | 8/2005 |
| EP | 1411836 B1 | 10/2005 |
| EP | 1 915 950 | 4/2008 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 A1 | 6/1999 |
| WO | WO 01/12257 A1 | 2/2001 |
| WO | WO 01/24869 A1 | 4/2001 |
| WO | WO 01/62158 A2 | 8/2001 |
| WO | WO 01/62162 A1 | 8/2001 |
| WO | WO 01/62333 A1 | 8/2001 |
| WO | WO 02/067785 A2 | 9/2002 |
| WO | WO 03/088845 | 10/2003 |
| WO | WO 03/094746 | 11/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

Search Report dated Jan. 28, 2008 for Application No. EP 07 25 4219.

* cited by examiner

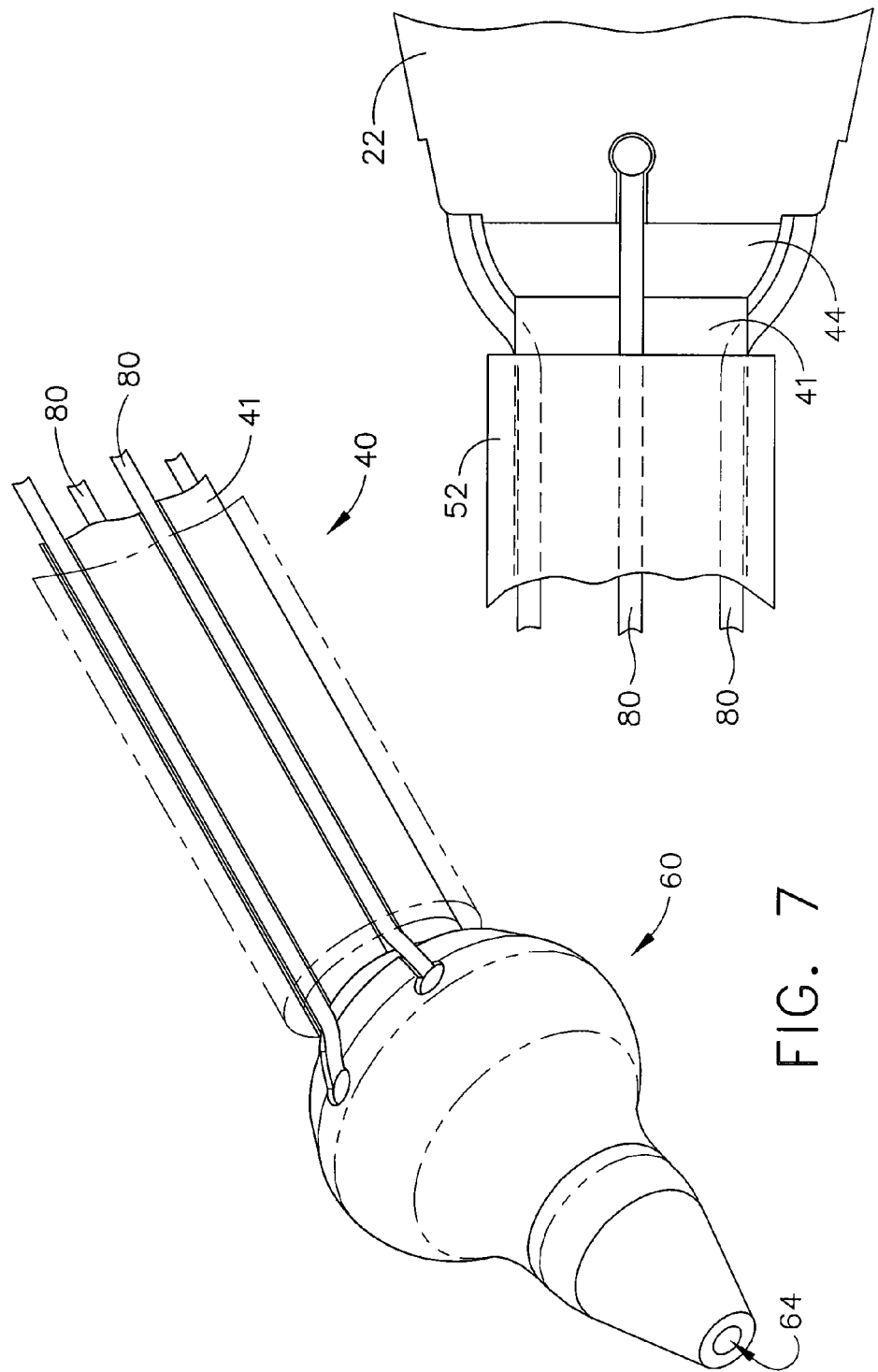

ADHESIVE APPLIER WITH ARTICULATING TIP

BACKGROUND

Biosurgical adhesives have been used in a variety of ways in various medical procedures. An exemplary adhesive is disclosed in U.S. Pub. No. 2004/0190975, the disclosure of which is incorporated by reference herein. Similarly, a variety of devices and techniques have been used to deliver adhesives at various sites. While several systems and methods have been made and used for delivering adhesives, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 6 depicts a partial plan view of an articulation joint of the adhesive applier of FIG. 1;

FIG. 7 depicts a perspective view of the distal end of the adhesive applier of FIG. 1;

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
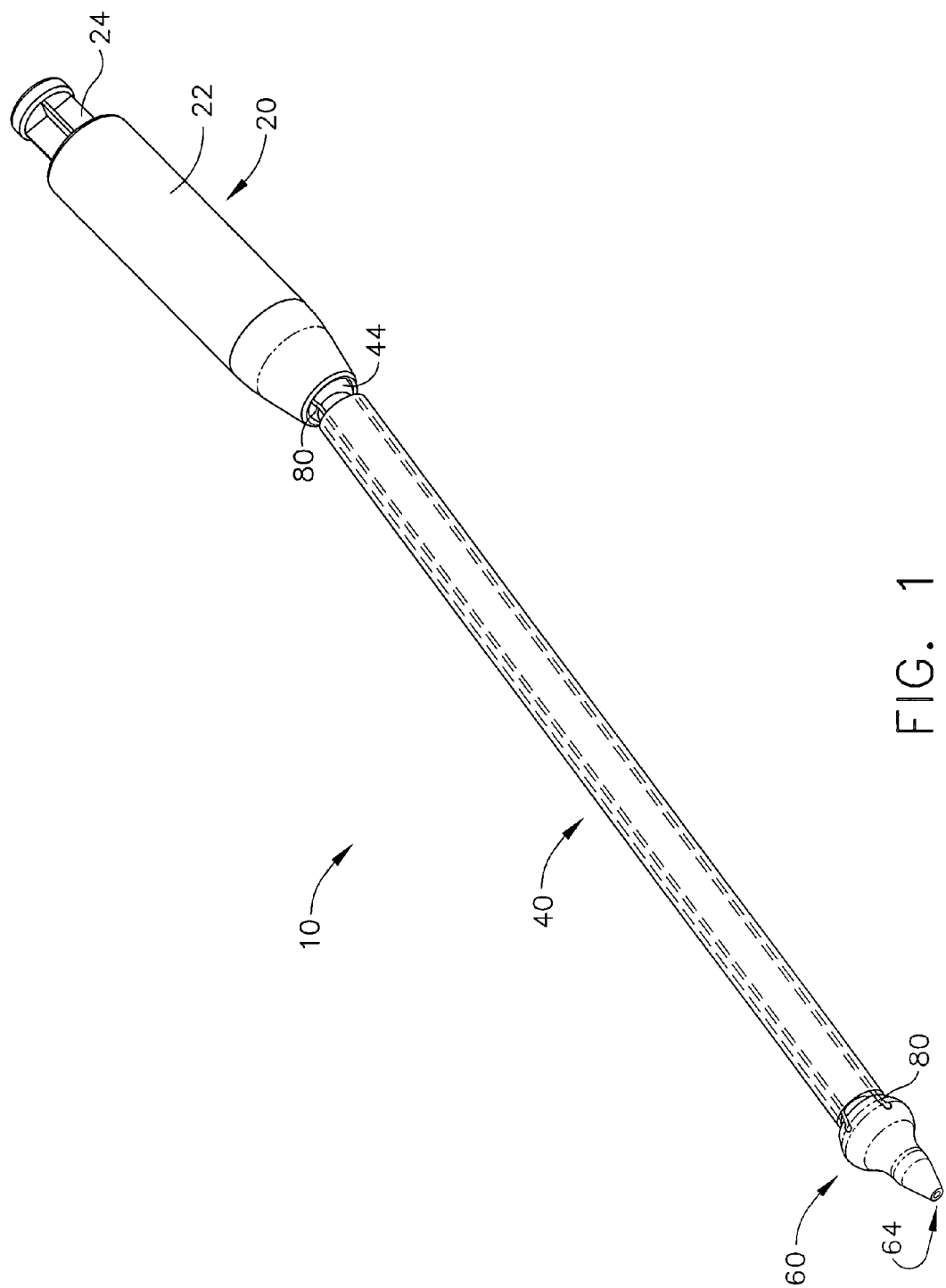
FIG. 1 depicts a perspective view of an exemplary adhesive applier.

As shown in FIG. 1, an exemplary adhesive applier (10) comprises a handle portion (20), a shaft portion (40), and a tip portion (60). A biosurgical adhesive is provided in handle portion (20). Handle portion (20) is operable to communicate adhesive to tip portion (60) via shaft portion (40). As will be described in greater detail below, handle portion (20) and tip portion (60) are each pivotally connected to shaft portion (40). In particular, applier (10) is configured such that pivoting of handle portion (20) relative to shaft portion (40) will effect pivoting of tip portion (60) relative to shaft portion (40). Applier (10) may thus be used to apply an adhesive at multiple angles relative to shaft portion (40).

In the present example, handle portion (20) comprises a barrel (22) and a plunger (24). Barrel (22) is configured to hold a liquid adhesive. By way of example only, such an adhesive may comprise a cyanoacrylate, an isocyanate, or any other suitable substance. Plunger (24) is operable to urge the adhesive through an opening (26) formed in the distal end of barrel (22). It will be appreciated that handle portion (20) is thus operable in a manner similar to a syringe. As will be described in greater detail below, a conduit (50) is disposed within opening (26), such that actuation of plunger (24) will effect communication of adhesive through conduit (50). Conduit (50) of the present example comprises a generally flexible tube. Handle portion (20) also has a socket (28), as will also be described in greater detail below. It will be appreciated that the foregoing components of handle portion (20) are merely exemplary, and that any of these components may be modified, substituted, supplemented, or omitted as desired. Suitable variations of handle portion (20) will be apparent to those of ordinary skill in the art. For instance, a variety of handle portion (20) types may be provided, such that a user may interchange such handle portions (20) relative to shaft portion (40) based on any suitable considerations (e.g., geometry of handle portion (20), contemplated use, etc.). For instance, in lieu of the barrel (22) and plunger (24) configuration, handle portion (20) may comprise a squeeze bulb, a pistol grip, a port for receiving a pressurized medium, or other features.

Shaft portion (40) comprises a shaft (41) having a distal ball (42), a proximal ball (44), and an interior lumen (46). Within each ball (42, 44), lumen (46) progressively widens outwardly to provide funnel-shaped portions (48). Conduit (50) extends through lumen (46). As will be described in greater detail, a plurality of push/pull cables (80) extend along longitudinal tracks (82) provided in shaft (41). A sheath (52) extends along shaft (41), and substantially encloses push/pull cables (80), thereby substantially restricting movement of cables (80) in a radial direction relative shaft (41). Tracks (82) substantially restrict transverse movement of cables (80) relative shaft (41), but permit longitudinal movement of cables (80). It will be appreciated that the foregoing components of shaft portion (40) are merely exemplary, and that any of these components may be modified, substituted, supplemented, or omitted as desired. Suitable variations of shaft portion (40) will be apparent to those of ordinary skill in the art. By way of example only, shaft portion (40) may be rigid (e.g., for open or laparoscopic uses), flexible (e.g., for endoscopic uses), or have other properties.

Proximal ball (44) of shaft (41) is inserted within socket (28) of handle portion (20). Accordingly, the resulting ball (44) and socket (28) joint between shaft portion (40) and handle portion (20) permits pivotal movement of handle portion (20) relative to shaft portion (40) in a variety of directions and at a variety of angles. Funnel-shaped portion (48) of lumen (46) in shaft (41) permits conduit (50) to flex with pivoting of handle portion (20) relative to shaft portion (40), substantially minimizing interference by shaft (41) relative to conduit (50) during such movement. In addition, cables (80) are secured to handle portion (20), such that pivotal movement of handle portion (20) relative to shaft portion (40) may be communicated along cables (80). In particular, and as will be described in greater detail below, pivotal movement of handle portion (20) relative to shaft portion (40) is communicated to tip portion (60) via cables (80) in the present example.

Tip portion (60) comprises a socket (62) and a distal opening (64). Distal ball (42) of shaft (41) is inserted in socket (62). Accordingly, the resulting ball (44) and socket (28) joint between shaft portion (40) and handle portion (20) permits pivotal movement of handle portion (20) relative to shaft portion (40) in a variety of directions and at a variety of angles. Cables (80) are secured to tip portion (60). Accordingly, as noted above, pivotal movement of handle portion (20) relative to shaft portion (40) is communicated to tip portion (60) via cables (80). In the present example, tip portion (60) mimics movement of handle portion (20) relative to shaft portion (40), though this may be limited or otherwise varied as desired. In the present example, funnel-shaped portion (48) of lumen (46) in shaft (41) permits conduit (50) to flex with pivoting of tip portion (60) relative to shaft portion (40), substantially minimizing interference by shaft (41) relative to conduit (50) during such movement.

Figure 2:
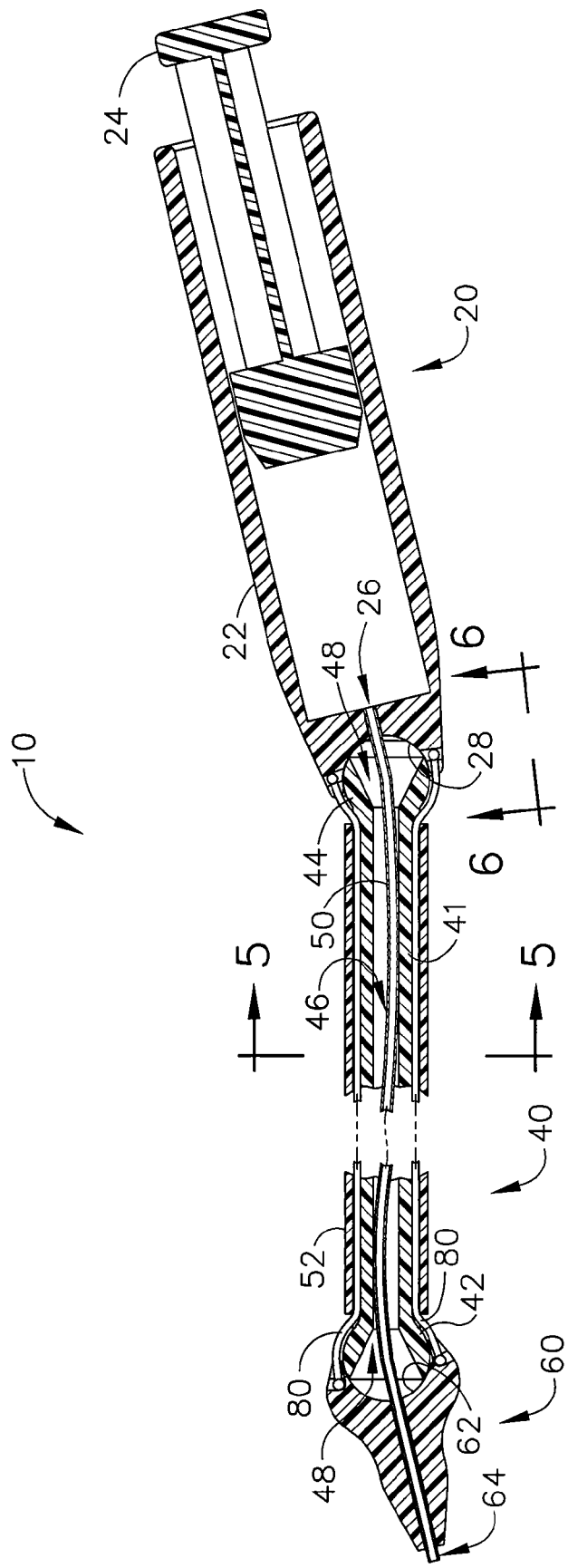
FIG. 2 depicts a cross-sectional view of the adhesive applier of FIG. 1.
Figure 3:
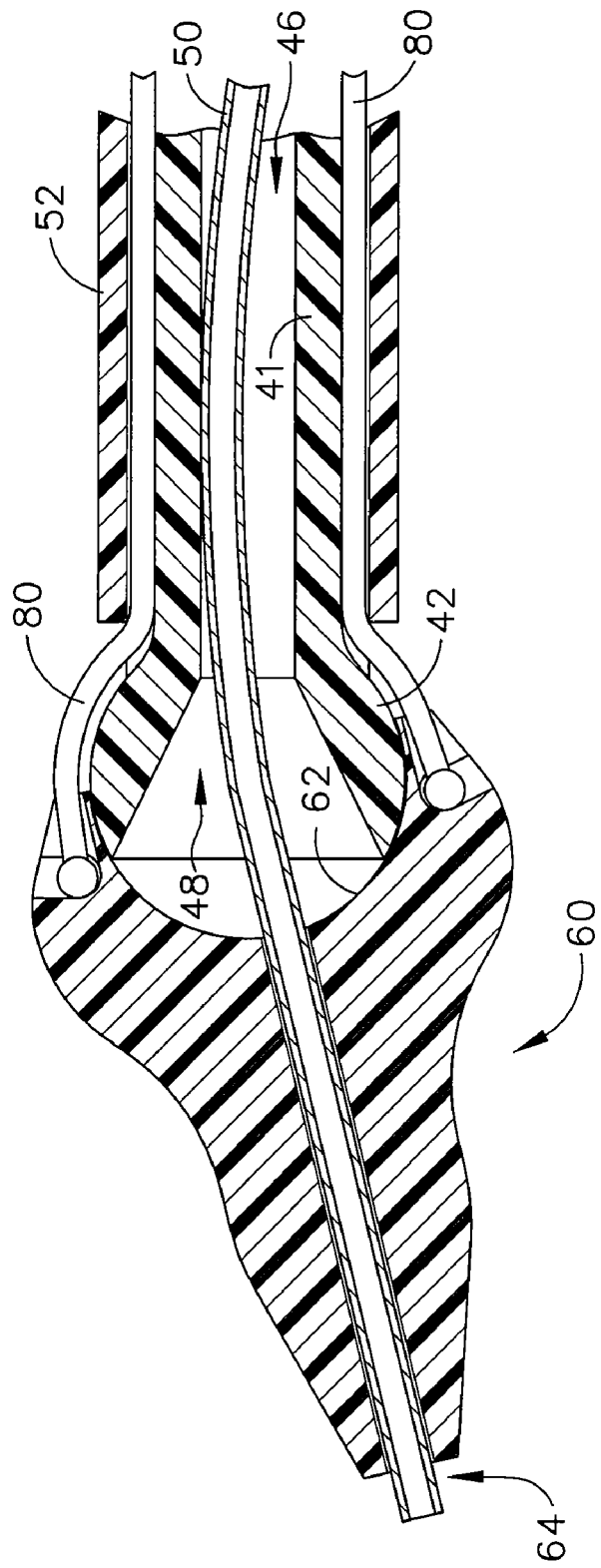
FIG. 3 depicts a partial cross-sectional view of the distal end of the adhesive applier of FIG. 1.
Figure 4:
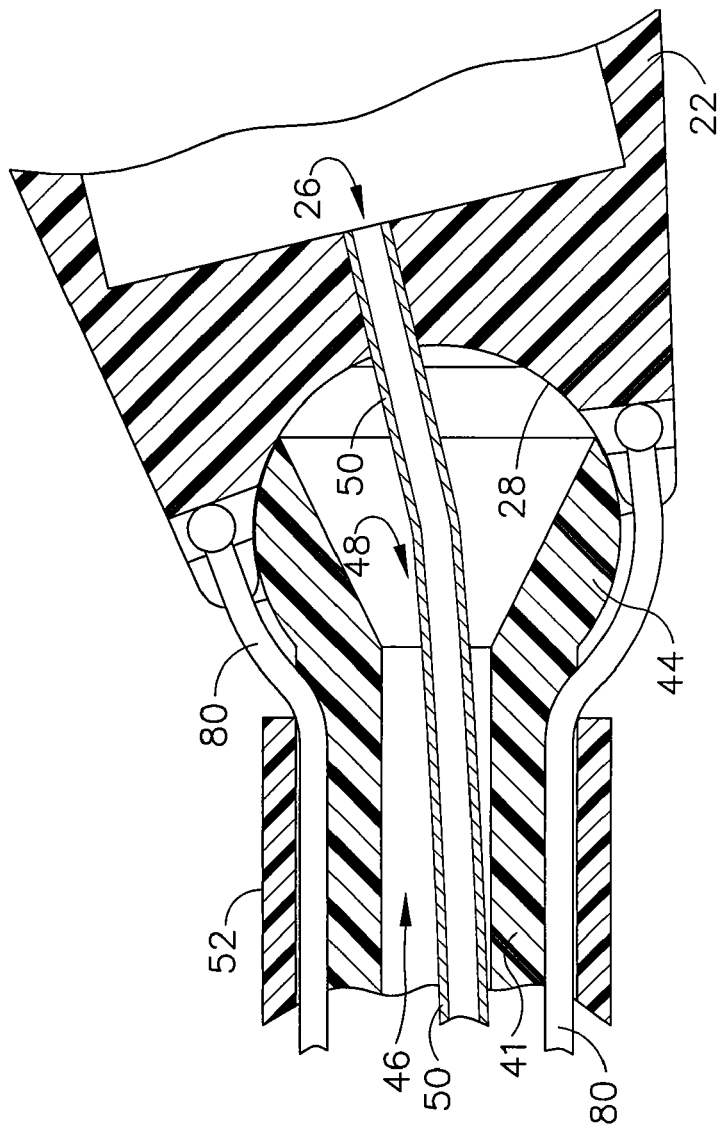
FIG. 4 depicts a partial cross-sectional view of an articulation joint of the adhesive applier of FIG. 1.
Figure 5:
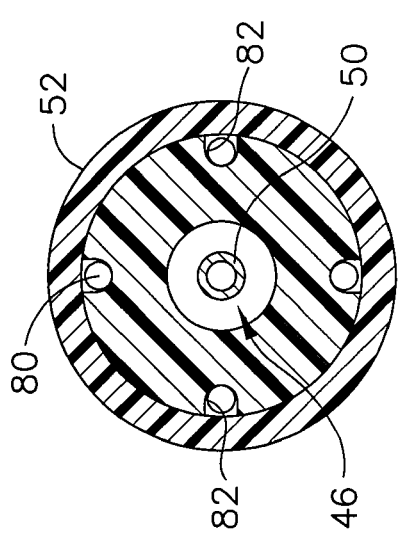
FIG. 5 depicts a cross-sectional view taken along line 5-5 of FIG. 2.
Figure 8:
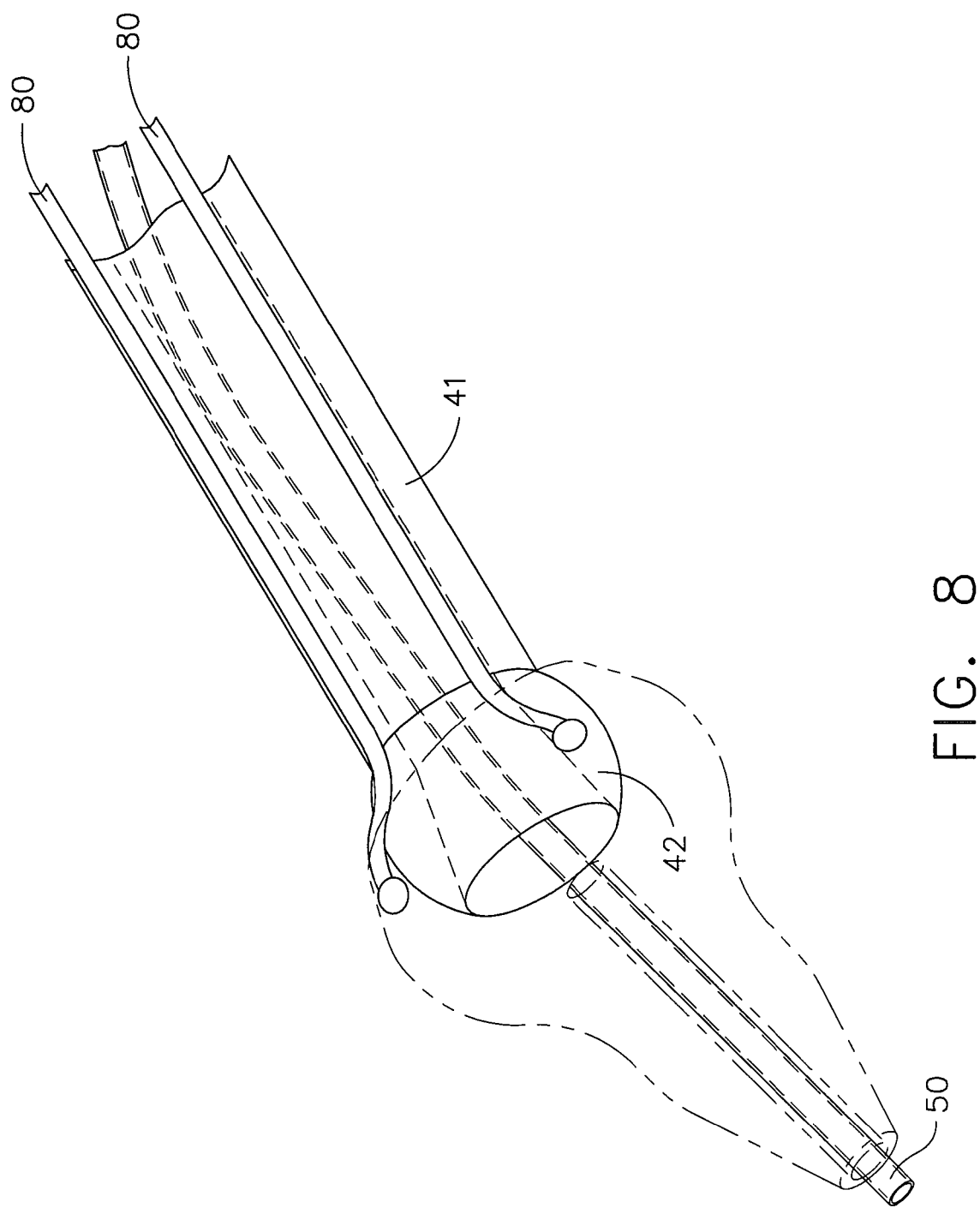
FIG. 8 depicts a perspective view of the distal end of a shaft portion of the adhesive applier of FIG. 1.
Figure 9:
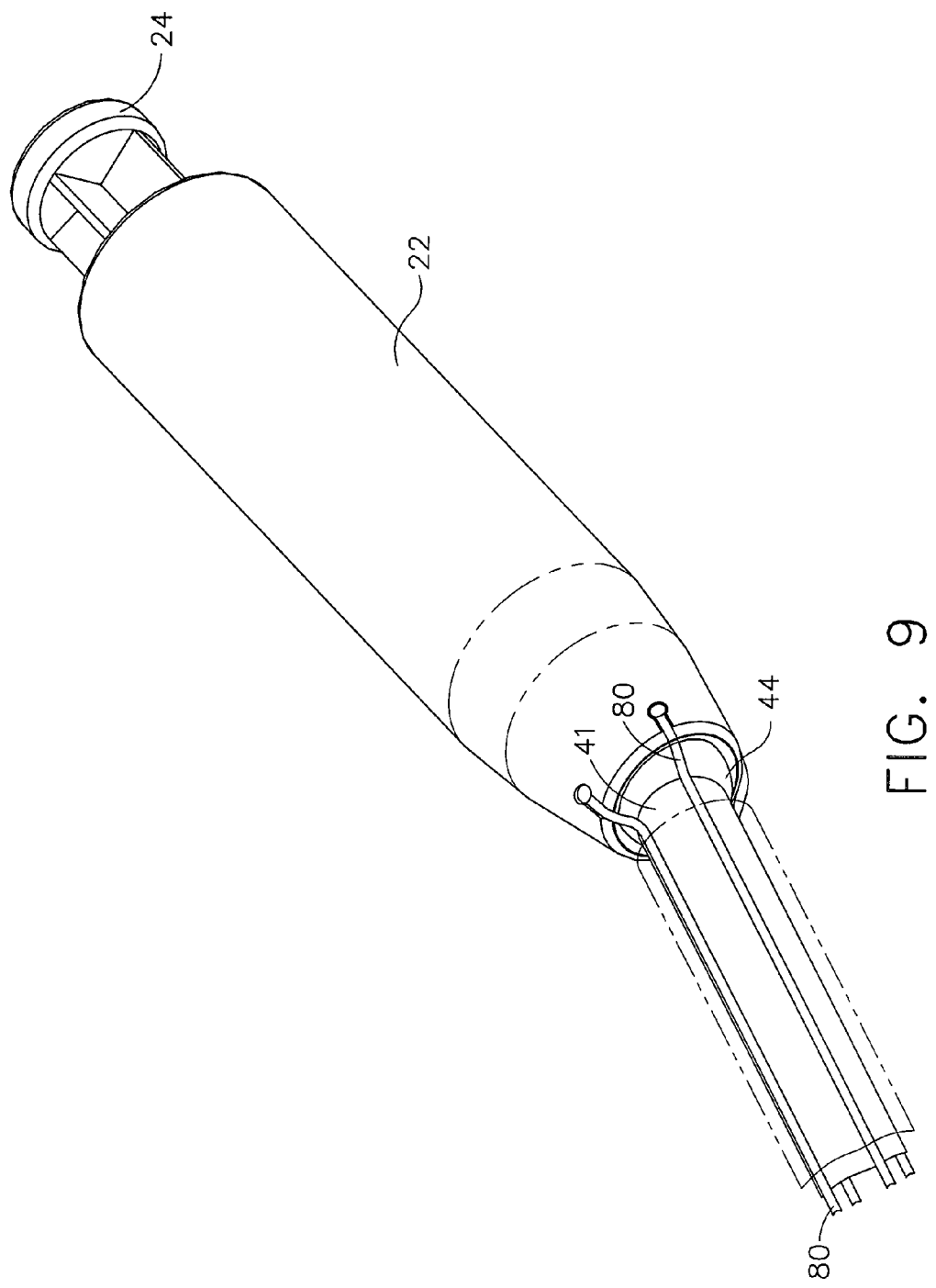
FIG. 9 depicts a perspective view of the proximal end of the adhesive applier of FIG. 1.

In the present example, adhesive is dispensed via distal opening (64) of tip portion (60). As shown in FIGS. 2-3 and 8, a portion of conduit (50) may extend distally from distal opening (64) of tip portion (60). Alternatively, conduit (50) may terminate within tip portion (60) or elsewhere. It will be appreciated that the foregoing components of tip portion (60) are merely exemplary, and that any of these components may be modified, substituted, supplemented, or omitted as desired. Suitable variations of tip portion (60) will be apparent to those of ordinary skill in the art. For instance, a variety of tip portion (60) types may be provided, such that a user may interchange such tip portions (60) relative to shaft portion (40) based on any suitable considerations (e.g., geometry of tip portion (60), contemplated use, etc.).

It will be appreciated that applier (10) of the present example may be subject to numerous modifications. By way of example only, additional degrees of freedom may be provided for handle portion (20) relative to shaft portion (40) and/or for tip portion (60) relative to shaft portion (40). In lieu of adhesives, applier (10) may be used to apply a variety of other substances, including but not limited to sealants, drugs, sclerosing agents, necrosing agents, coagulants, ablation agents, image enhancing agents such as ultrasound, CT, MRI, PET, X-Ray (radiographic), or radio pharmaceuticals. Other substances will be apparent to those of ordinary skill in the art. An applier (10) may also be provided with one or more features that is/are operable to selectively lock the position/orientation of tip portion (60) relative shaft portion (40) and/or the position/orientation of handle portion (20) relative shaft portion (40).

In addition, while articulation or pivoting of tip portion (60) and handle portion (20) relative to shaft portion (40) is described herein as being manual, it will also be appreciated that such articulation or pivoting may be mechanized or otherwise automated at least in part. Suitable features for providing such mechanization or automation will be apparent to those of ordinary skill in the art. It will also be appreciated that any suitable alternative to cables (80) may be provided, including but not limited to rods. Similarly, while four cables (80) are shown, any other suitable number of cables (80) or cable (80) alternatives may be used (e.g., one, two, or three, etc.).

While ball (42, 44) and socket (62, 28) joints are shown, any other types of joints may be used. For instance, hinges, universal joints, or pivoting joints, etc., may be used. In another embodiment, the ball (44) and socket (28) joint between handle portion (20) and shaft portion (40) is eliminated. In this variation, articulation of tip portion (60) relative shaft portion (40) is effected by movement of a stick, slider(s), or other feature operable to effect communication of motion to tip portion (60). Other suitable joints and features operable to effect motion at one or more joints will be apparent to those of ordinary skill in the art.

While the present example contemplates an adhesive or other substance being provided within handle portion (20), it is also contemplated that such adhesive or other substance may alternatively be provided in either or both of shaft portion (40) or tip portion (60). Similarly, different substances may be provided in different portions of applier (10). For instance, an adhesive may be provided within handle portion (20), while an adhesive activator may be provided within tip portion (60). Furthermore, while the present example contemplates user input being provided via handle portion (20), user input may alternatively or additionally be provided via other structures.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An adhesive applier, comprising:
(a) a handle portion having a proximal end and a distal end, wherein the handle portion is configured to be gripped by a user, wherein the handle portion comprises a barrel and a plunger, wherein the plunger extends proximally from the barrel;
(b) a liquid substance within the barrel;
(c) a shaft portion having a proximal end and a distal end, wherein the shaft portion defines an inner lumen;
(d) a first ball and socket joint coupling the distal end of the handle portion with the proximal end of the shaft portion, such that the handle portion is pivotable relative to the shaft portion, wherein the first ball and socket joint comprises a first ball and a first socket, wherein the first ball has an interior funnel-shaped portion in communication with the lumen;
(e) a tip portion having a proximal end and a distal end;
(f) a second ball and socket joint coupling the distal end of the shaft portion with the proximal end of the tip portion, such that the tip portion is pivotable relative to the shaft portion, wherein the second ball and socket joint comprises a second ball and a second socket, wherein the second ball has an interior funnel-shaped portion in communication with the lumen;
(g) a conduit in fluid communication with the barrel, wherein the conduit extends through the interior funnel-shaped portion of the first ball, through the lumen, through the interior funnel-shaped portion of the second ball, and through the tip portion, wherein the handle portion is operable to cause dispensation of the liquid substance via the conduit at the distal end of the tip portion in response to actuation of the plunger by a user; and
(h) at least one cable connecting the handle portion with the tip portion, such that the at least one cable is configured to cause the tip portion to pivot relative the shaft portion in response to pivoting of the handle portion relative to the shaft portion;
wherein the interior funnel-shaped portion of the first ball is configured to permit the conduit to flex to reduce interference between the conduit and the first ball and the first socket during pivoting of the handle portion relative to the shaft portion at the first ball and socket joint;
wherein the interior funnel-shaped portion of the second ball is configured to permit the conduit to flex to reduce interference between the conduit and the second ball and the second socket during pivoting of the tip portion relative to the shaft portion at the second ball and socket joint.

2. The adhesive applier of claim 1, wherein the liquid substance comprises an adhesive.

3. The adhesive applier of claim 2, wherein the adhesive comprises one or both of a cyanoacrylate or an isocyanate.

4. The adhesive applier of claim 1, wherein movement of the tip portion relative to the shaft portion in response to movement of the handle portion relative to the shaft portion mimics the movement of the handle portion relative to the shaft portion.

5. The adhesive applier of claim 1, wherein the conduit comprises a flexible tube.

6. A method of applying and adhesive, the method comprising:
(a) providing a liquid substance applier, wherein the liquid substance applier comprises:
  (i) a handle portion having a proximal end and a distal end, wherein the handle portion is configured to be gripped by a user,
  (ii) a shaft portion having a proximal end and a distal end, wherein the shaft portion defines an inner lumen,
  (iii) a first ball and socket joint coupling the distal end of the handle portion with the proximal end of the shaft portion, such that the handle portion is pivotable relative to the shaft portion, wherein the first ball and socket joint comprises a first ball and a first socket, wherein the first ball has an interior funnel-shaped portion in communication with the lumen, and
  (iv) a tip portion having a proximal end and a distal end,
  (v) a second ball and socket joint coupling the distal end of the shaft portion with the proximal end of the tip portion, such that the tip portion is pivotable relative to the shaft portion, wherein the second ball and socket joint comprises a second ball and a second socket, wherein the second ball has an interior funnel-shaped portion in communication with the lumen,
  (vi) a conduit in fluid communication with the handle portion, wherein the conduit extends through the interior funnel-shaped portion of the first ball, through the lumen, through the interior funnel-shaped portion of the second ball, and through the tip portion, wherein the handle portion is operable to cause dispensation of a liquid substance via the conduit at the distal end of the tip portion, and
  (vii) at least one cable connecting the handle portion with the tip portion, such that the at least one cable is configured to cause the tip portion to articulate relative the shaft portion in response to pivoting of the handle portion relative to the shaft portion,
wherein the interior funnel-shaped portion of the first ball is configured to permit the conduit to flex to reduce interference between the conduit and the first ball and the first socket during pivoting of the handle portion relative to the shaft portion at the first ball and socket joint,
wherein the interior funnel-shaped portion of the second ball is configured to permit the conduit to flex to reduce interference between the conduit and the second ball and the second socket during pivoting of the tip portion relative to the shaft portion at the second ball and socket joint;
(b) providing a liquid substance within the handle portion of the liquid substance applier;
(c) grasping the handle portion;
(d) positioning the tip portion at a surgical site, wherein the step of positioning the tip portion comprises articulating the tip portion relative to the shaft portion at the second ball and socket joint, wherein the step of articulating the tip portion comprises pivoting the handle portion relative to the shaft portion at the first ball and socket joint, such that pivotal movement of the handle portion relative to the shaft portion is communicated along the at least one cable; and
(e) dispensing at least a portion of the liquid substance in the handle portion at the surgical site via the conduit through the interior funnel-shaped portion of the first ball, through the lumen, through the interior funnel-shaped portion of the second ball, and through distal end of the articulated tip portion.

7. The method of claim 6, wherein the liquid substance comprises a surgical adhesive.

8. The method of claim 6, wherein the handle portion comprises a plunger and a barrel, wherein the act of dispensing comprises actuating the plunger.

9. An adhesive applier device, comprising:
(a) a handle portion having a proximal end and a distal end, wherein the handle portion is configured to be gripped by a user;

(b) a liquid substance provided within the handle portion;

(c) a shaft portion having a proximal end and a distal end, wherein the shaft portion defines an inner lumen;

(d) a first ball and socket joint coupling the distal end of the handle portion with the proximal end of the shaft portion, such that the handle portion is pivotable relative to the shaft portion, wherein the first ball and socket joint comprises a first ball and a first socket, wherein the first ball has an interior funnel-shaped portion in communication with the lumen;

(e) a tip portion having a proximal end and a distal end;

(f) a second ball and socket joint coupling the distal end of the shaft portion with the proximal end of the tip portion, such that the tip portion is pivotable relative to the shaft portion, wherein the second ball and socket joint comprises a second ball and a second socket, wherein the second ball has an interior funnel-shaped portion in communication with the lumen;

(g) a conduit in fluid communication with the handle portion, wherein the conduit extends through the interior funnel-shaped portion of the first ball, through the lumen, through the interior funnel-shaped portion of the second ball, and through the tip portion, wherein the handle portion is operable to cause dispensation of the liquid substance via the conduit at the distal end of the tip portion; and (h) at least one cable connecting the handle portion with the tip portion, such that the cable is configured to cause the tip portion to pivot relative the shaft portion in response to pivoting of the handle portion relative to the shaft portion;

wherein the interior funnel-shaped portion of the first ball is configured to permit the conduit to flex to reduce interference between the conduit and the first ball and the first socket during pivoting of the handle portion relative to the shaft portion at the first ball and socket joint;

wherein the interior funnel-shaped portion of the second ball is configured to permit the conduit to flex to reduce interference between the conduit and the second ball and the second socket during pivoting of the tip portion relative to the shaft portion at the second ball and socket joint.

\* \* \* \* \*